United States Patent [19]
Kroll et al.

[11] Patent Number: 5,531,770
[45] Date of Patent: Jul. 2, 1996

[54] DEVICE AND METHOD FOR DETERMINING DEFIBRILLATION THRESHOLDS

[75] Inventors: Mark W. Kroll, Minnetonka; Gary L. McQuilkin, Plymouth; Kai C. Kroll, Minnetonka, all of Minn.

[73] Assignee: Angeion Corporation, Plymouth, Minn.

[21] Appl. No.: 115,736

[22] Filed: Sep. 3, 1993

[51] Int. Cl.⁶ ................................................ A61N 1/39
[52] U.S. Cl. ............................................................. 607/8
[58] Field of Search ......................................... 607/4–8, 28

[56] References Cited

U.S. PATENT DOCUMENTS

| | | | |
|---|---|---|---|
| 4,708,142 | 11/1982 | DeCote, Jr. | 607/28 |
| 4,895,152 | 1/1990 | Callaghan et al. | 607/28 |
| 5,105,809 | 4/1992 | Bach, Jr. et al. | 607/5 |

OTHER PUBLICATIONS

Wyse et al., "Comparison of biphasic and Monophasic Shocks for Defibrillation Using a Nonthoracotomy System", *The American Journal of Cardiology* vol. 71, Jan. 15, 1993, 197–202.

*Primary Examiner*—William E. Kamm
*Attorney, Agent, or Firm*—Patterson & Keough

[57] ABSTRACT

A method for rapidly and accurately determining defibrillation thresholds. The method comprises the steps of delivering an initial shock series to a patient, the shock series comprising at least two shocks of differing energy levels, determining an estimated shock level adjustment based on the initial shock series, and delivering at least one adjusted shock of a predetermined energy level based on the estimated shock level adjustment. The technique uses optimized search criteria as opposed to the conventional step-wise decrease and increase techniques. An apparatus for implementing the method is also disclosed.

15 Claims, 16 Drawing Sheets

| CENTER OF GRAVITY | | JUMP GAIN= | 0.00 | |
|---|---|---|---|---|
| COUNTS | 16 | 3 | 0.00 | |
| | SUCCESS | FAILURE | ESTIMATE | RANDOM |
| | 10.10 | 8.79 | 9.44 | 8.50 |
| 7.50 | 15.00 | 7.50 | | |
| 15.00 | 11.25 | 9.55 | | |
| 11.25 | 10.31 | 9.31 | | |
| 10.31 | 9.84 | | | |
| 9.84 | 10.06 | | | |
| 9.55 | 9.91 | | | |
| 10.06 | 9.79 | | | |
| 9.91 | 9.70 | | | |
| 9.79 | 9.63 | | | |
| 9.70 | 9.57 | | | |
| 9.63 | 9.52 | | | |
| 9.57 | 9.47 | | | |
| 9.52 | 9.43 | | | |
| 9.47 | 9.40 | | | |
| 9.43 | 9.37 | | | |
| 9.40 | 9.34 | | | |
| 9.37 | | | | |
| 9.34 | | | | |
| 9.31 | | | | |
| 9.31 | | | | |
| 9.44 | | | | |

FIG. 8

| CENTER OF GRAVITY | | JUMP GAIN= | 0.25 | |
|---|---|---|---|---|
| COUNTS | 22 | 12 | -0.46 | |
| | SUCCESS | FAILURE | ESTIMATE | RANDOM |
| | 9.22 | 8.53 | 8.42 | 7.90 |
| 7.50 | 15.00 | 7.50 | | |
| 15.00 | 11.25 | 9.01 | | |
| 11.25 | 9.81 | 8.46 | | |
| 9.81 | 9.76 | 8.79 | | |
| 9.01 | 9.36 | 8.44 | | |
| 9.76 | 9.02 | 8.58 | | |
| 9.36 | 8.73 | 8.68 | | |
| 9.02 | 8.99 | 8.61 | | |
| 8.73 | 8.84 | 8.67 | | |
| 8.46 | 8.70 | 8.55 | | |
| 8.79 | 8.57 | 8.60 | | |
| 8.99 | 8.76 | 8.50 | | |
| 8.84 | 8.68 | | | |
| 8.70 | 8.73 | | | |
| 8.57 | 8.67 | | | |
| 8.44 | 8.61 | | | |
| 8.58 | 8.64 | | | |
| 8.68 | 8.59 | | | |
| 8.76 | 8.55 | | | |
| 8.68 | 8.54 | | | |
| 8.61 | 8.49 | | | |
| 8.67 | 8.45 | | | |
| 8.73 | | | | |
| 8.67 | | | | |
| 8.61 | | | | |
| 8.55 | | | | |
| 8.60 | | | | |
| 8.64 | | | | |
| 8.59 | | | | |
| 8.55 | | | | |
| 8.50 | | | | |
| 8.54 | | | | |
| 8.49 | | | | |
| 8.45 | | | | |

FIG. 10

| CENTER OF GRAVITY | | JUMP GAIN= | 1.00 | |
|---|---|---|---|---|
| COUNTS | 11 | 11 | 0.00 | |
| | SUCCESS | FAILURE | ESTIMATE | RANDOM |
| | 9.88 | 7.89 | 8.88 | 7.13 |
| 7.50 | 15.00 | 7.50 | | |
| 15.00 | 11.25 | 8.31 | | |
| 11.25 | 10.52 | 6.75 | | |
| 8.31 | 8.58 | 7.39 | | |
| 10.52 | 7.62 | 7.79 | | |
| 8.58 | 9.07 | 7.36 | | |
| 7.62 | 7.74 | 7.58 | | |
| 6.75 | 9.97 | 8.75 | | |
| 7.39 | 10.01 | 8.82 | | |
| 7.79 | 8.89 | 7.72 | | |
| 9.07 | 9.98 | 8.83 | | |
| 7.74 | | | | |
| 7.36 | | | | |
| 7.58 | | | | |
| 8.75 | | | | |
| 9.97 | | | | |
| 8.82 | | | | |
| 10.01 | | | | |
| 8.89 | | | | |
| 7.72 | | | | |
| 8.83 | | | | |
| 9.98 | | | | |

FIG. 12

| | CENTER OF GRAVITY | JUMP GAIN= | 0.70 | |
|---|---|---|---|---|
| | COUNTS | 12 | 12 | 0.00 | |
| | SUCCESS | FAILURE | ESTIMATE | RANDOM |
| | 9.33 | 7.78 | 8.56 | 8.57 |
| 7.50 | 15.00 | 7.50 | | |
| 15.00 | 11.25 | 7.51 | | |
| 11.25 | 8.91 | 7.16 | | |
| 8.91 | 8.56 | 7.68 | | |
| 7.51 | 7.82 | 8.01 | | |
| 8.56 | 8.94 | 7.99 | | |
| 7.82 | 8.86 | 7.96 | | |
| 7.16 | 8.80 | 7.93 | | |
| 7.68 | 8.74 | 7.72 | | |
| 8.01 | 7.90 | 7.67 | | |
| 8.94 | 7.82 | 7.75 | | |
| 7.99 | 9.32 | 8.52 | | |
| 8.86 | | | | |
| 7.96 | | | | |
| 8.80 | | | | |
| 7.93 | | | | |
| 8.74 | | | | |
| 7.90 | | | | |
| 7.72 | | | | |
| 7.82 | | | | |
| 7.67 | | | | |
| 7.75 | | | | |
| 8.52 | | | | |
| 9.32 | | | | |

FIG. 14

DEVICE AND METHOD FOR DETERMINING DEFIBRILLATION THRESHOLDS

BACKGROUND OF THE INVENTION

1. Technical Field

This invention relates to medical therapeutic apparatus and methods and more particularly to a method and apparatus for use in conjunction with a cardioverter-defibrillator, for example an implantable cardioverter-defibrillator, to determine the defibrillation threshold thereof. The method and apparatus of the present invention enables the safe and accurate determination of defibrillation thresholds.

2. Background Information

Defibrillation of the human heart is accomplished by passing a large current pulse through it. It is important to know the parameters of such a pulse for both research and clinical reasons. A common parameter of the strength of the pulse is its energy measured in joules (J). Additional parameters are current, voltage, or time adjusted (effective) current.

In research on defibrillation, knowledge of the amount of energy required to defibrillate the heart allows the evaluation of various waveforms, drugs, electrodes and the like. In the clinical application it is extremely important to know this amount of energy, commonly called the defibrillation threshold (DFT), in order to ascertain that the defibrillator device, for example an implantable defibrillator, has sufficient energy to defibrillate a patient's heart. An implantable defibrillator should have a significant reserve of energy or "safety margin." It is also important to know the patient's DFT in order to set the output of the device at a reasonable value which will defibrillate without wasting battery energy and without doing unnecessary harm to the heart by over-shocking.

The determination of the DFT is not a trivial matter as there is no precise and absolute threshold at which determination is always 100% successful above the threshold and 100% unsuccessful for energies below it. And, studies have shown that the potential for causing brain damage exists from exceeding 6 defibrillation shocks for DFT determination purposes. Thus, it is important to minimize the number of shocks used in its determination. Referring to FIG. 1, it has been found that there is a "dose response" function. In this example, a patient has a 0% chance of being defibrillated with shocks of 4 joules (J) and a 100% chance of being defibrillated with a shock of 12 J with a gradual slope occurring between 6 and 10 J. Points at which 50% to 70% success rates are expected have typically been defined as the DFT. Without loss of generality, the 50% point is used in this discussion, although the teachings of this invention are readily adapted to other definitions.

A simulated success-dosage curve is shown in FIG. 2 for the purpose of evaluating various prior art DFT determination techniques. In this example, there is a linear response in the chance of success between 6 J and 10 J and the chance of success goes from 0.0 to a probability 1.00. The true DFT is 8 J, which will be utilized for purposes of comparing the performance of all of the examples below. This curve gives a rather severe test of DFT determination algorithms and serves to highlight the differences in their performances.

The flow chart shown in FIG. 3 shows a conventional approach to DFT determination, namely the "Bourland Algorithm." In this approach, the heart is fibrillated and a very high energy shock is delivered. If that shock is successful or positive, the energy level is decreased in fixed size steps. This step-wise decrease in energy levels continues until it is no longer possible to fibrillate the heart and the experiment is stopped. The lowest successful energy level is recorded as the DFT. One variant of the Bourland approach or protocol is to use a smaller step size and reverse the direction after the first failure to defibrillate the heart. Although the Bourland approach has been found to be easy to implement, it does not give accurate determinations. It suffers from two problems. The first is that there is a wide error band around the true DFT. The second is that there is a fixed error referred to as a "statistical bias" in that the Bourland protocol will tend to overestimate the threshold. This has been shown to be due to the fact that the Bourland protocol starts at a high energy and comes down. As soon as a failure is encountered, the algorithm stops, or even reverses, and thus it tends to give high DFT estimates.

Another variant on the Bourland protocol is the so-called Bourland "Triple Determination" Method. In this technique, the standard protocol is merely repeated three times and the average DFT value is recorded as the "true" DFT. An example of this approach is shown in FIG. 4a using the simulated defibrillation response of FIG. 2. In this simulation, the initial energy level was 15 J and this was decreased one step at a time until a failure was noted. Of course, no failure would be expected until the energy level was below 10 J. The 9 J shock was a failure and thus the first determination gave a threshold of 10 J. Beginning again, a 12 J shock was delivered which was successful, followed by successful 11, 10, and 9 J shocks and a failure at 8 J. This gave 9 J for the threshold in this second determination. Beginning again, a 12 J shock was successful as were shocks of 11, 10, 9, 8, and 7 J. A 6 J shock failed. The average of the three determinations is 8.75 J. A total of 19 shocks were required to finish the determination which was 9% above the true DFT.

Because of the inaccuracies and large number of shocks required with the Bourland approach, the "Three Reversal" method has been recently proposed. This method is similar to the Bourland Triple Determination process with two differences. The first difference is that after a failure, the energy level is increased by 1 J increments. The second difference is that the calculation does not merely average three successful levels, but rather averages all values since the first failure as well as the last successful shock before the failure, and an "implied result" at the very end of the process. FIG. 4b shows the results of a simplified version of the three reversal method. A determination starts at 15 J. The shock energy was reduced to 7 J before the first failure occurred. The energy was then increased to 8 J, at which point success occurred. Had there been no success at 8 J the energy level would have been further increased to 9 J. Since there was a success at 8 J the energy level was then reduced to 7 J. The shock was successful at 7 J so the energy was then reduced to 6 J which failed. At this point it is assumed that the next high level shock, namely one at 7 J, would be successful and it is not performed. It is however included in the average. Thus the calculation averages the numbers 8, 7, 8, 7, 6, 7 to arrive at a DFT determination of 7.17 J. This represents an error of 10% and would have required 12 shocks to determine.

The only known improvement that has been made on the up/down-type techniques discussed above is the "Binary Search" method. In this approach, one either increases or decreases the estimated energy level based on whether or not the previous shock was a failure or success, respectively, but always cuts the estimation interval in half. An example of this approach is shown in FIG. 5. This approach has only been implemented with human interaction and thus the numbers have been kept simple. This technique is disclosed in *Comparison of Biphasic and Monophasic Shocks for Defibrillation Using a Non-thoracotomy System*, American Journal of Cardiology, 1993, Volume 71, pages 197–202. The first shock is always 20 J. If that fails then 30 J is used. If it succeeds then 10 J is used.

Referring to FIG. 5, using our test model of an 8 J threshold, the Binary Search method was utilized wherein the first shock was at 20 J which was successful. The next shock was one half this level (10 J), and was also successful. This was then halved to a 5 J level which was a failure. Cutting the interval in half again yields 7.5 J level which was successful. The half-way point between the 5 J and 7.5 J levels is 6.25 J which was a failure. This process was continued and arrived at a DFT estimate of 7.18 J after 12 shocks. This approach is potentially a very dangerous approach as it gives a false confidence of accuracy. The graph in FIG. 5 shows a rapid convergence to a stable value. However this calculated DFT value of 7.18 J is 10% below the correct threshold of 8 J and this accuracy would not increase regardless of how many additional shocks are used. The problem with the binary search technique is that even one "unlucky" shock result will destroy the accuracy for all following shock attempts. In the instant example, the 7.5 J shock was successful. As a result, the estimate had to be less then 7.5 J and thus could never converge to the appropriate value of 8 J.

As is apparent from the comparison of prior art techniques above, there is a need for a device and method for rapidly and accurately estimating the defibrillation threshold. The method must feature a robust approach which allows increasing accuracy with an increasing number of shocks and yet with reasonable accuracy with a minimal number of shocks. A device is also required for implementing the method in that the optimal estimation method involves some calculations which must be solved via processing means as opposed to human manipulation.

SUMMARY OF THE INVENTION

The present invention provides a method for determining defibrillation thresholds, comprising the steps of:

a) delivering an initial shock series to a patient, the shock series comprising a first shock of a predetermined energy level which yields either a positive or negative defibrillation event, and at least one successive shock of an increasing or decreasing energy level, respectively, at least one negative and one positive defibrillation event, respectively, is yielded;

b) determining an estimated shock level adjustment, the determination being made by adding a midpoint estimation and a jump factor, the midpoint estimation being an estimate of all previously delivered shocks, and the jump factor representing an adjustment away from the midpoint estimation; the midpoint estimation being determined by determining the mean of all negative defibrillation event shock, determining the mean of all positive defibrillation event shocks, and by determining the average of the determined negative mean and positive mean, the jump factor being determined according to:

Jump Factor=$G_j(C_f/C_s-1)(M_s-M_f)$, if $C_f$ is $\geq C_s$; and $-G_j(C_s/C_f-1)(M_s-M_f)$, if $C_s$ is $>C_f$, wherein $M_f$=mean of negative defibrillation event shock energy levels, $M_s$=mean of positive defibrillation event shock energy levels, $C_f$=count of negative defibrillation event shocks, $C_s$=count of positive defibrillation event shocks, and $G_j$=jump constant;

c) delivering an adjusted shock of a predetermined energy level based on the estimated shock level adjustment, and d) determining whether the adjusted shock meets predetermined stopping criteria and concluding the method if the stopping criteria are met, the adjusted shock being a defibrillation threshold, and repeating steps (b)–(d), sequentially, if the stopping criteria are not met, whereby the successive shocks converge on the defibrillation threshold by continuously varying estimated shock level adjustments via a statistical analysis.

The invention further provides an apparatus for determining defibrillation thresholds, comprising:

a) charge storage means;

b) a fast charging circuit;

c) switch means;

d) electrode connection means;

e) a microprocessor based control circuit, including program instructions for implementing the above-described method, and f) means to connect the control circuit to positive/negative defibrillation event detection means.

It is the principle object of this invention to provide a device and method which significantly improves the determination of DFT's. The present invention can determine DFT's to an accuracy of 10% by typically using no more than 5 shocks. With the use of more shocks the invention allows a more accurate determination of the DFT with errors of 2–4 percent after 15–20 shocks.

These and other benefits of this invention will become clear from the following description by reference to the drawings.

BRIEF DESCRIPTION OF THE DRAWINGS

FIGS. 8 and 9 show a data table and graph, respectively, of estimated results using the method of the present invention, wherein the jump gain equals zero (0);

FIGS. 10 and 11 show a data table and graph, respectively, of estimated results using the method of the present invention, wherein the jump gain equals 0.25;

FIGS. 12 and 13 show a data table and graph, respectively, of estimated results using the method of the present invention, wherein the jump gain equals 1.0;

FIGS. 14 and 15 show a data table and graph, respectively, of estimated results using the method of the present invention, wherein the jump gain equals 0.7;

DESCRIPTION OF THE PREFERRED EMBODIMENT

Figure 1:
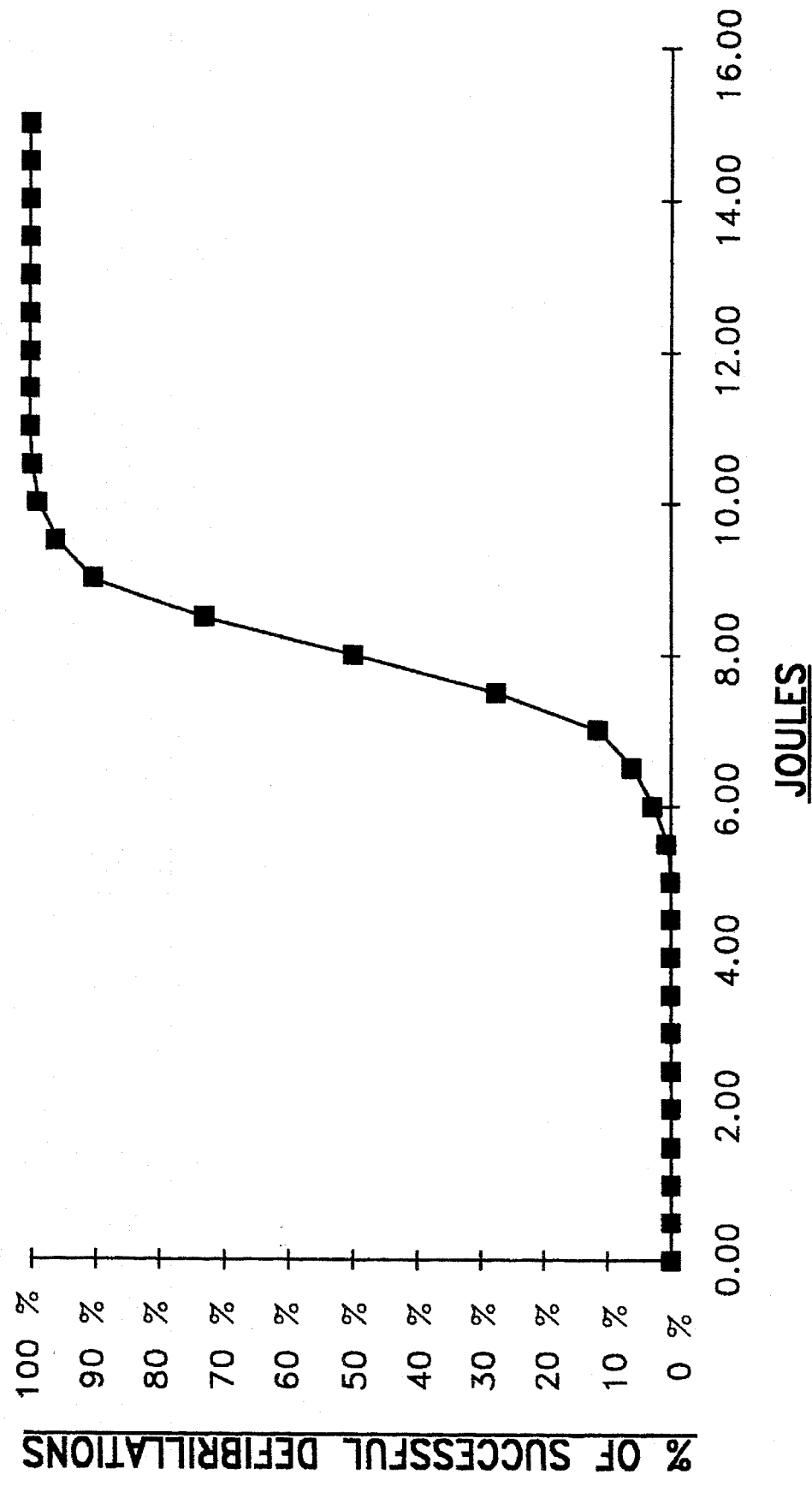
FIG. 1 is a graph showing the typical success-dosage curve for human defibrillation threshold determination, wherein the "X" axis represents the magnitude of energy of a defibrillation shock (dosage) in joules and the "Y" axis represents the percentage of successful defibrillations for a given shock.
Figure 2:
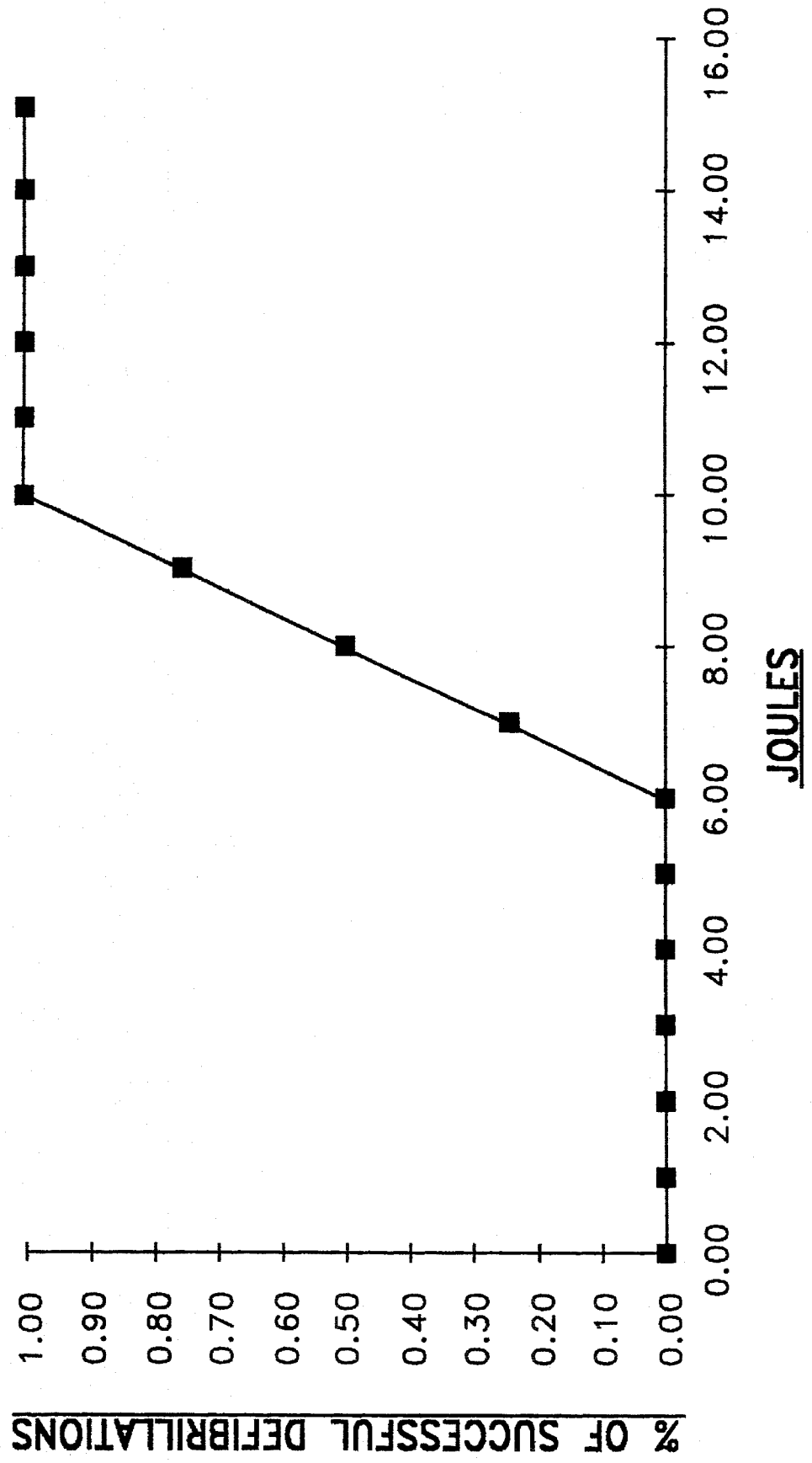
FIG. 2 is a graph showing a simulated success-dosage curve for use in comparing DFT determination techniques.
Figure 3:
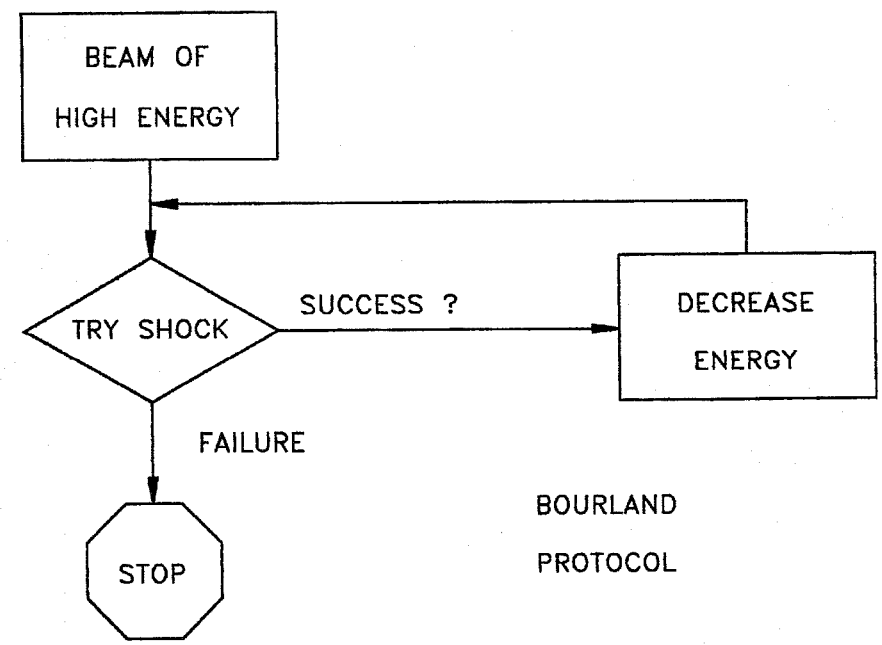
FIG. 3 is a flow chart showing the prior art Bourland Protocol of DFT determination.
Figure 4A:
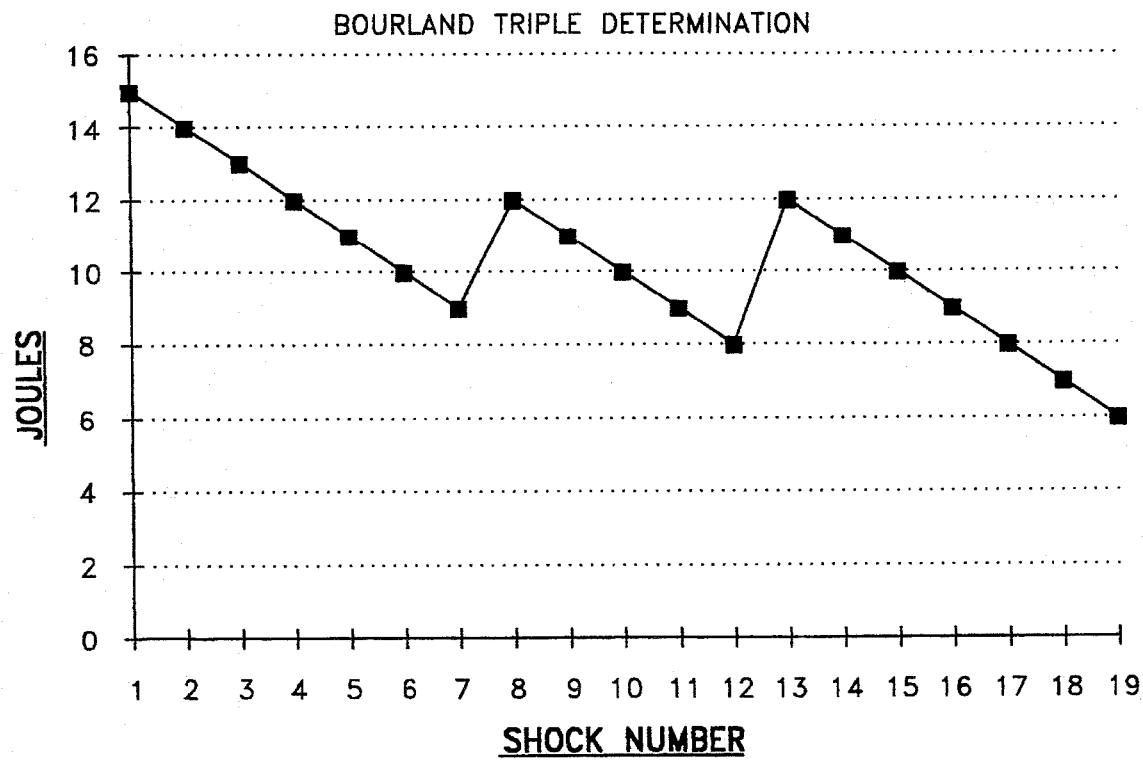
FIG. 4a is a graph showing an example of the prior art Bourland Triple Determination Method.
Figure 4B:
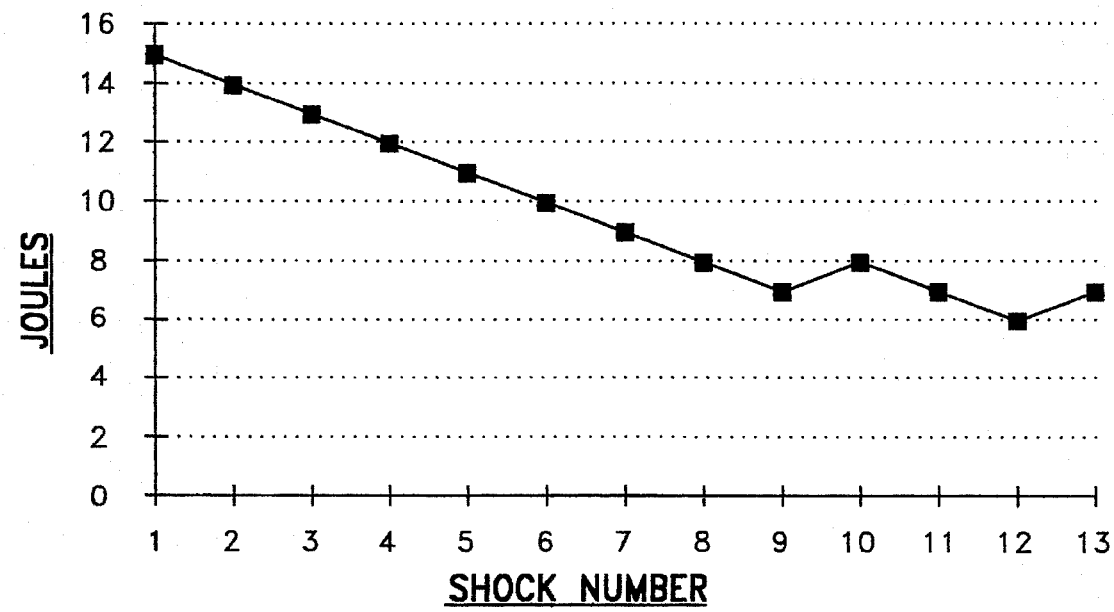
FIG. 4b is a graph showing an example of the prior art Boutland Three Reversal Method.
Figure 5:
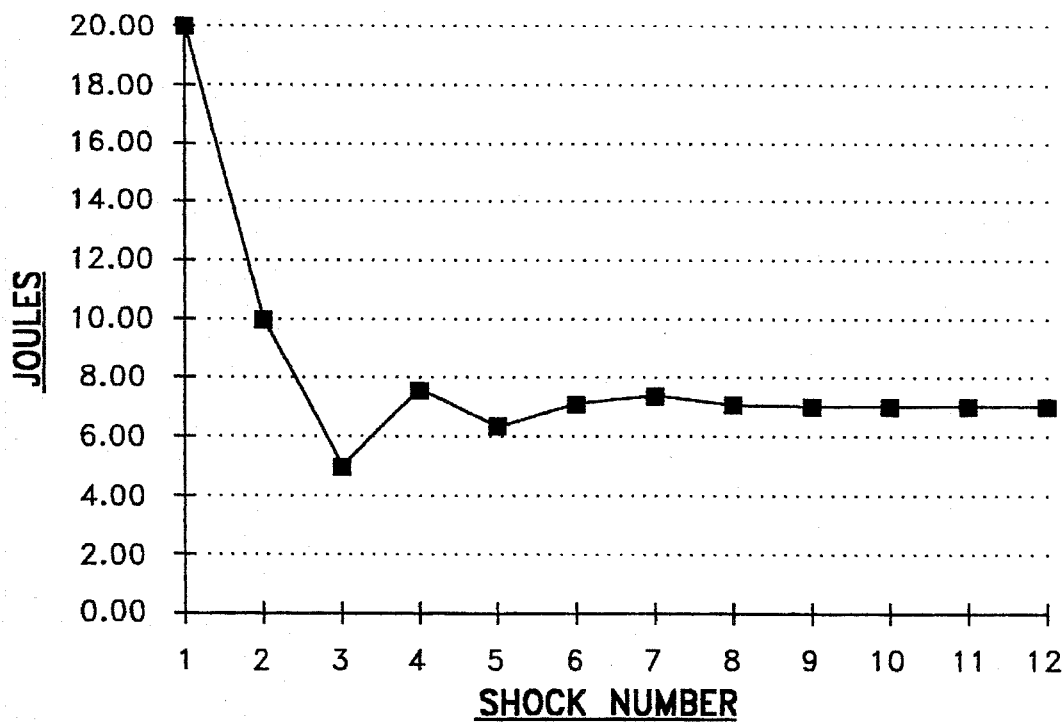
FIG. 5 is a graph showing an example of the prior art Binary Search Method.
Figure 6:
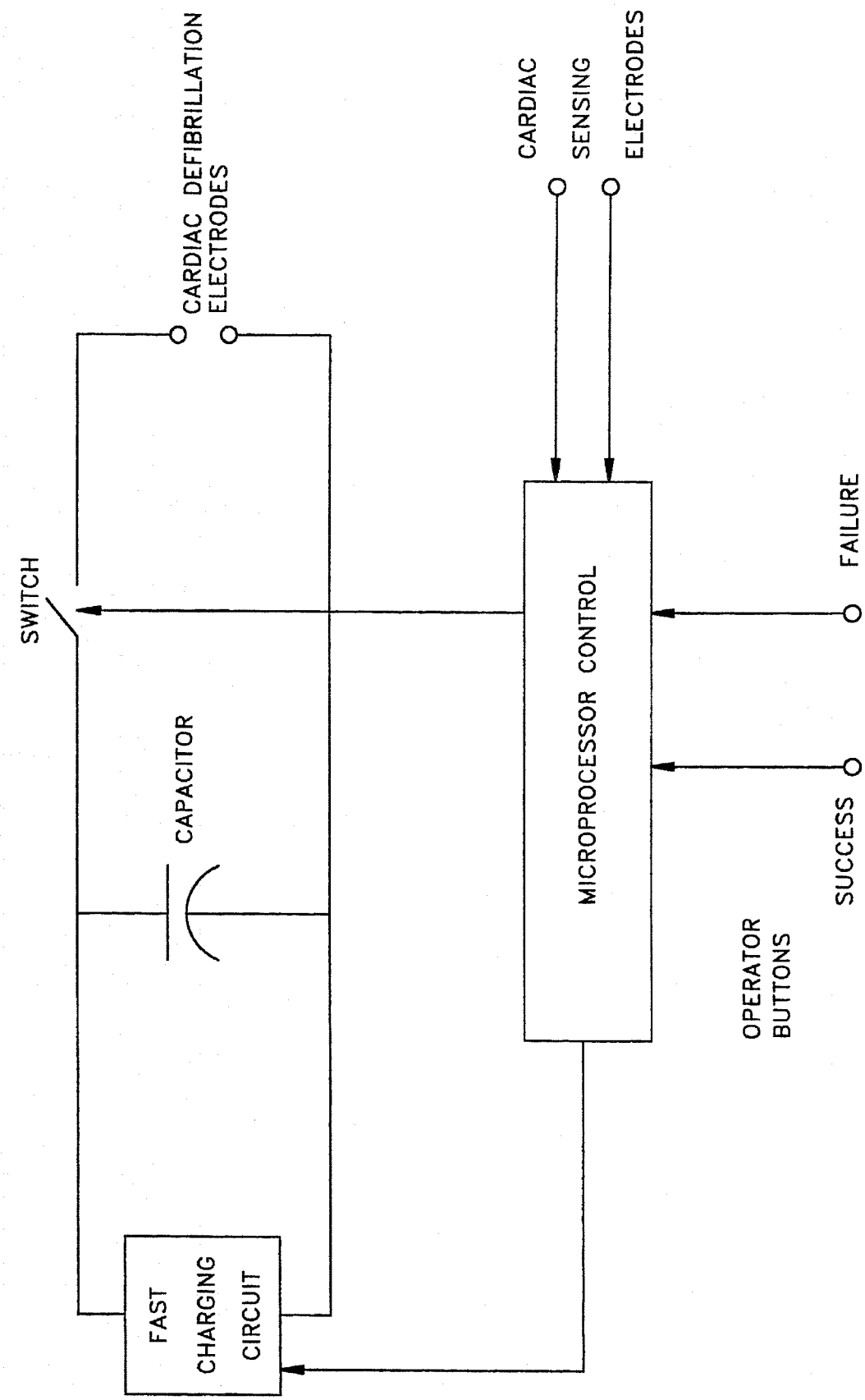
FIG. 6 is a schematic diagram of the apparatus for determining defibrillation thresholds of the present invention.

Referring to FIG. 6 the apparatus 10 of this invention basically comprises a fast charging circuit 11, a capacitor 12 which stores defibrillation shock energy, and a switch 13 which delivers the capacitor 12 energy to the patient's heart through the cardiac defibrillation electrodes 14a and b. The fast charging circuitry 11 and the switch 13 are both controlled by a microprocessor control block 15. This block has inputs 16a and b from cardiac sensing electrodes or operator buttons 17a and b. It is important for the control block 15 to receive information as to whether or not a defibrillation shock has been successful or is a failure. This could either be determined by the automatic analysis of electrogram signals from the cardiac sensing electrodes. In the alternative, success/failure detection may be determined from the operator signaling either a success (positive) or failure (negative) via the control buttons 17a and b.

Figure 7:
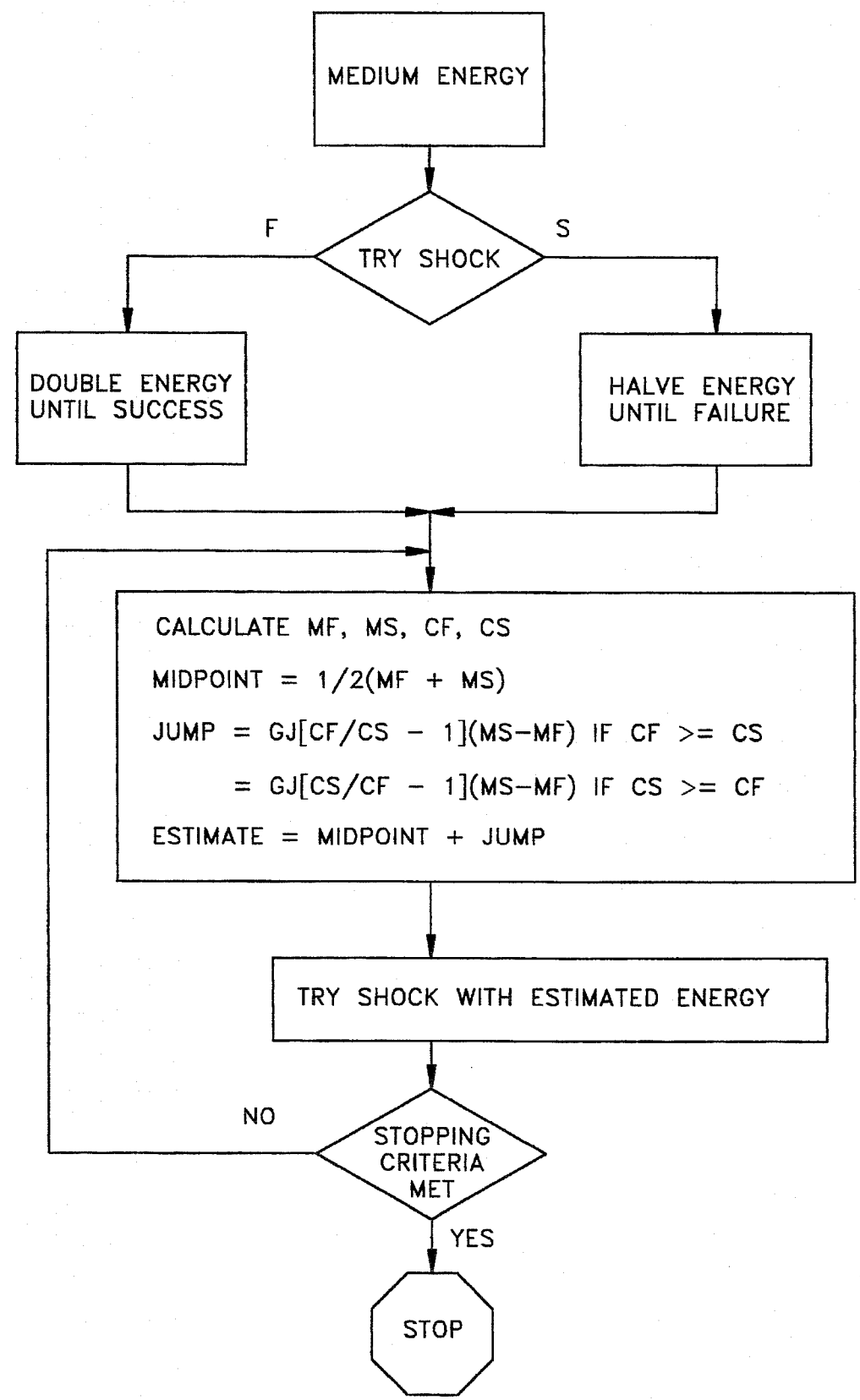
FIG. 7 is a flow chart of the method for determining defibrillation thresholds of the present invention.

The method of this invention, which is implemented via the apparatus 10, is set forth in the flow chart shown in FIG. 7. The important aspect of the method of the invention is the use of a convergence technique, which involves the establishment of a base history of shocks and then adjusting the level of the shock energy in varying step sizes to find the DFT.

The method of the invention begins with the delivery of a first shock of medium energy level. If the first shock is a failure or positive defibrillation event, one or more shocks are delivered, the energy levels of which are doubled from the immediately preceding shock, until a successful shock or positive defibrillation event is obtained. If the first shock is successful, then shock administration is continued with energy levels which are halved with respect to the immediately preceding shock, until a failure is encountered. This phase of the process concludes, therefore, upon detecting a shock outcome change with respect to that of the initial shock. This initial series of shocks provides a base history from which accurate adjustment may be made to the DFT.

After this initial phase is completed, the following parameters are calculated:

1. $M_f$=mean of failed (negative) shock energies;
2. $M_s$=mean of successful (positive) shock energies;
3. $C_f$=count of failed shocks; and
4. $C_s$=count of successful shocks.

These parameters are then utilized to calculate the following parameters:

5. Midpoint=½×($M_f$+$M_s$)

6a. Jump Factor = $G_j (C_f/C_s - 1)(M_s - M_f)$, if $C_f \geqq C_s$; and

6b. = $-G_j (C_s/C_f - 1)(M_s - M_f)$, if $C_s > C_f$;

wherein $G_f$ represents "jump gain" which is a constant by which the system determines to jump away from a series of estimates.

Parameters 5 and 6a and b are then used to calculate an Estimated Energy Level for the next shock, according to:

7. Estimated Energy Level=Midpoint+Jump Factor.

The midpoint calculation provides an estimate for a succeeding shock which is based on the midpoint of the mean of the failed shocks and the mean of the successful shocks administered in the first phase of the method. This approach alone will not necessarily converge to the correct answer as it is possible that a high energy shock will fail and thus the midpoint estimates will always be too high to decrease into the failure zone. The jump factor represents the magnitude of adjustment of the estimated shock from the midpoint.

Figure 9:
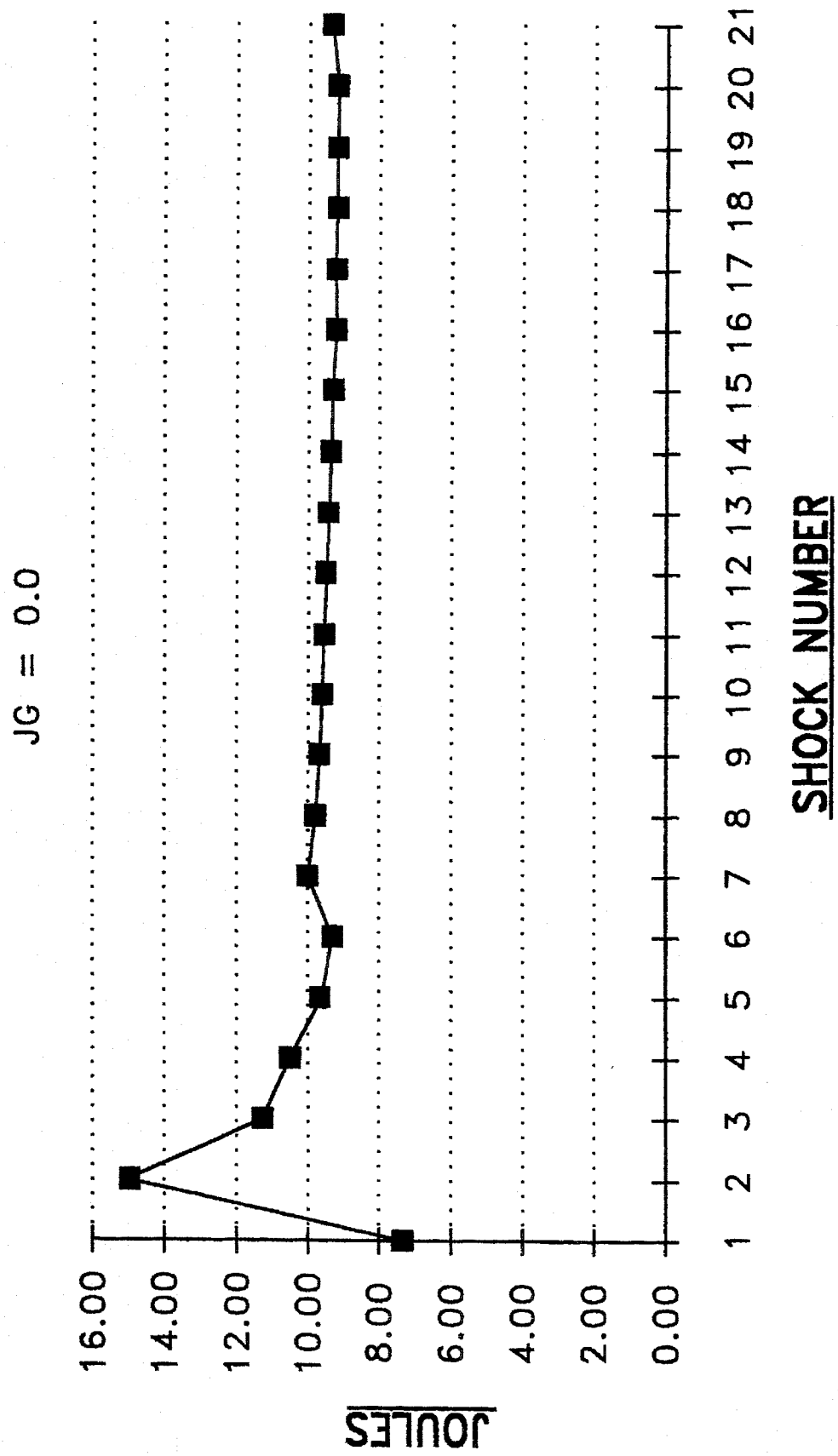

The next shock is now conducted with the estimated energy level. Stopping criteria are then checked to determine whether additional shocks are required. The method and device can be set to either attain a fixed level of accuracy or a fixed (maximum) number of shocks, for example via the stopping criteria. If the stopping criteria are not met, then the procedure continues and one or more shocks are delivered sequentially. After each shock in the series, the above-referenced calculations are repeated to determine an estimated level for the next shock. If the stopping criteria are met after any shock, then the method stops. FIGS. 8 and 9 show exemplary results of this method wherein a jump gain ($G_j$) of 0 is utilized. This example demonstrates that the basic midpoint approach alone will not necessarily work. The first column is the shock history, the 2nd is the successes, and the third is the failures. The initial shock energy value is set at 7.5 J as it will be throughout the following examples. This initial shock fails so the energy level is doubled to 15 J. The shock administered at this level is successful. The midpoint is now the average of 7.5 J and 15 J, namely 11.25 J. The 11.25 J energy value is tried and is a success. The average successful shock now is, 13.13 J. The midpoint of 13.13 J and 7.5 J is 10.31 J, which is then utilized for the next shock and is a success. This procedure is continued and it is noted that even after 21 shocks the estimates are all above 9 J. As is best shown in FIG. 9, merely relying on the midpoints do not allow the algorithm to "jump" out of an inaccurate trap. Hence, the algorithm failed to converge to the correct DFT of 8 J.

Figure 11:
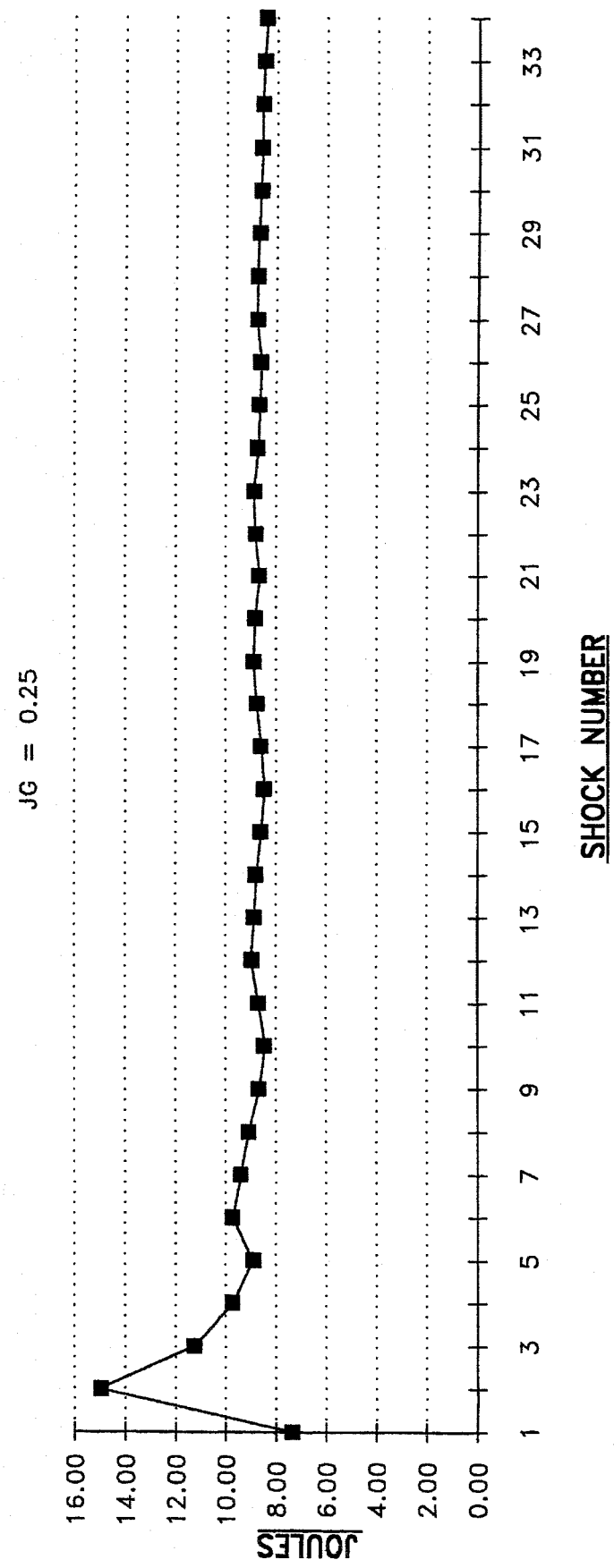

FIGS. 10 and 11 show experimental results based on the use of a jump gain of 0.25. Estimates within 1 J of the correct 8 J value are achieved after only 9 shocks. However, it is noted that after 34 shocks, the accuracy is still not significantly improved. This suggests that the jump gain of 0.25 is insufficient to "pull" the later estimates away from a bad early estimate.

Figure 13:
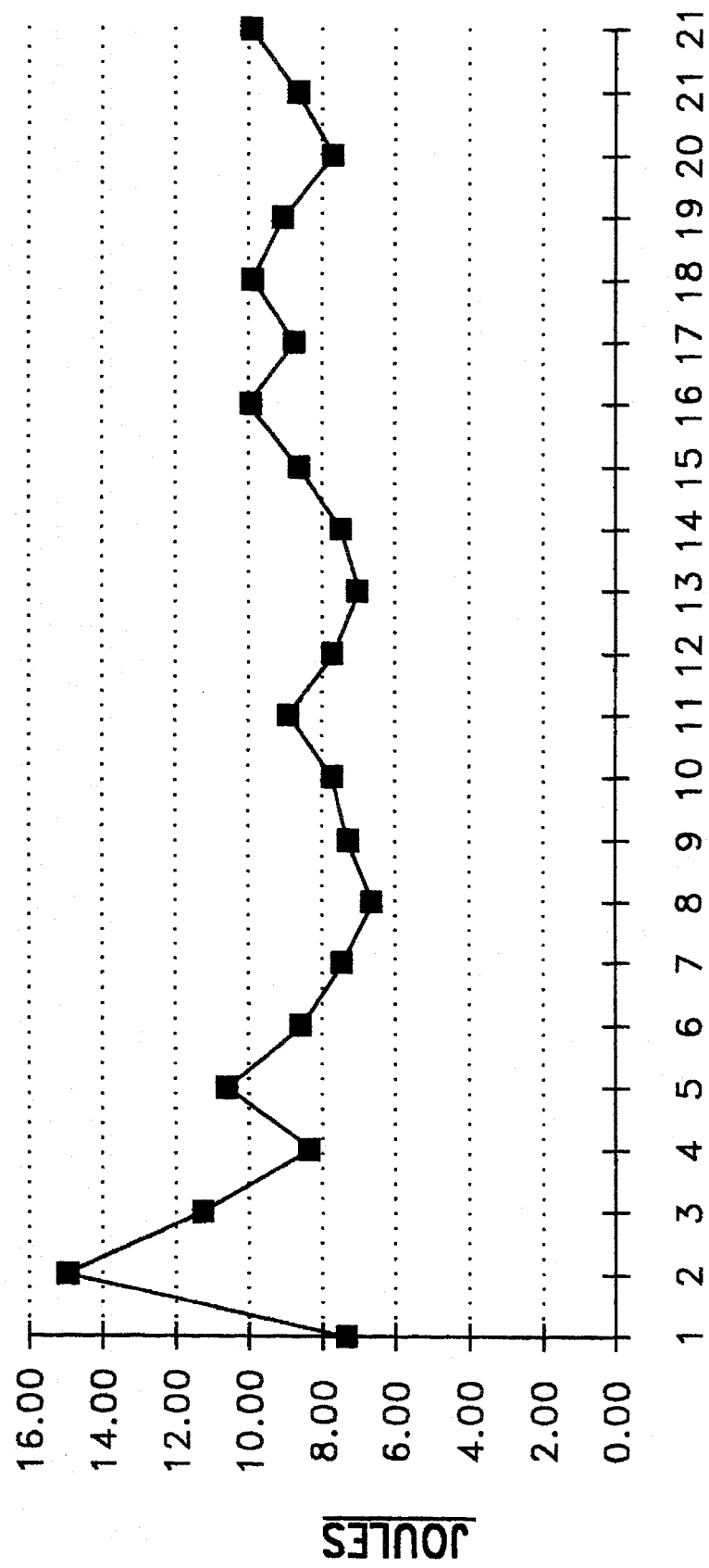

FIGS. 12 and 13 show the use of a jump gain of 1.00. The forth estimate is reasonably accurate at 8.31 J. However, there is an excessive gain in this system in that the estimates never settle to a stable value. Estimate No. 22 was actually 9.98 J while estimate No. 20 was 7.72 J. This suggests that a jump gain of 1 is excessive.

Figure 15:
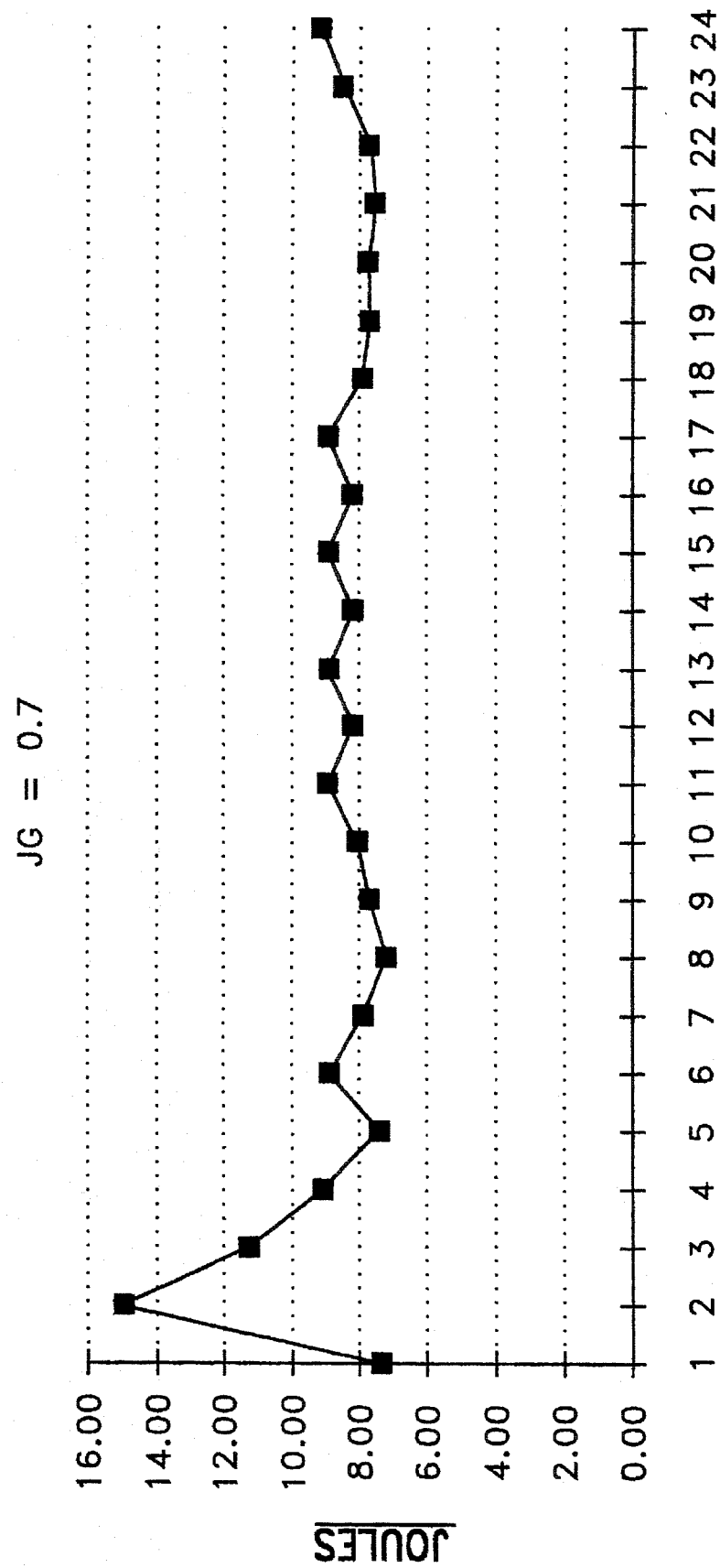

FIGS. 14 and 15 depict results with a jump gain of 0.7. Again, the estimates fail to settle, and instead remain oscillatory until shock No. 18. The estimates appear to be stable for five shocks and then they begin to climb again giving an estimate of 9.32 J after shock No.24.

Referring again to FIG. 7, the jump calculation shows the ratio of successes to failures by dividing the count of successful shocks $C_s$ by the count of failed shocks $C_f$. When this calculation indicates that there is an imbalance between the success and failure shocks then it forces a jump in the energy to get closer to the less represented region.

Figure 16:
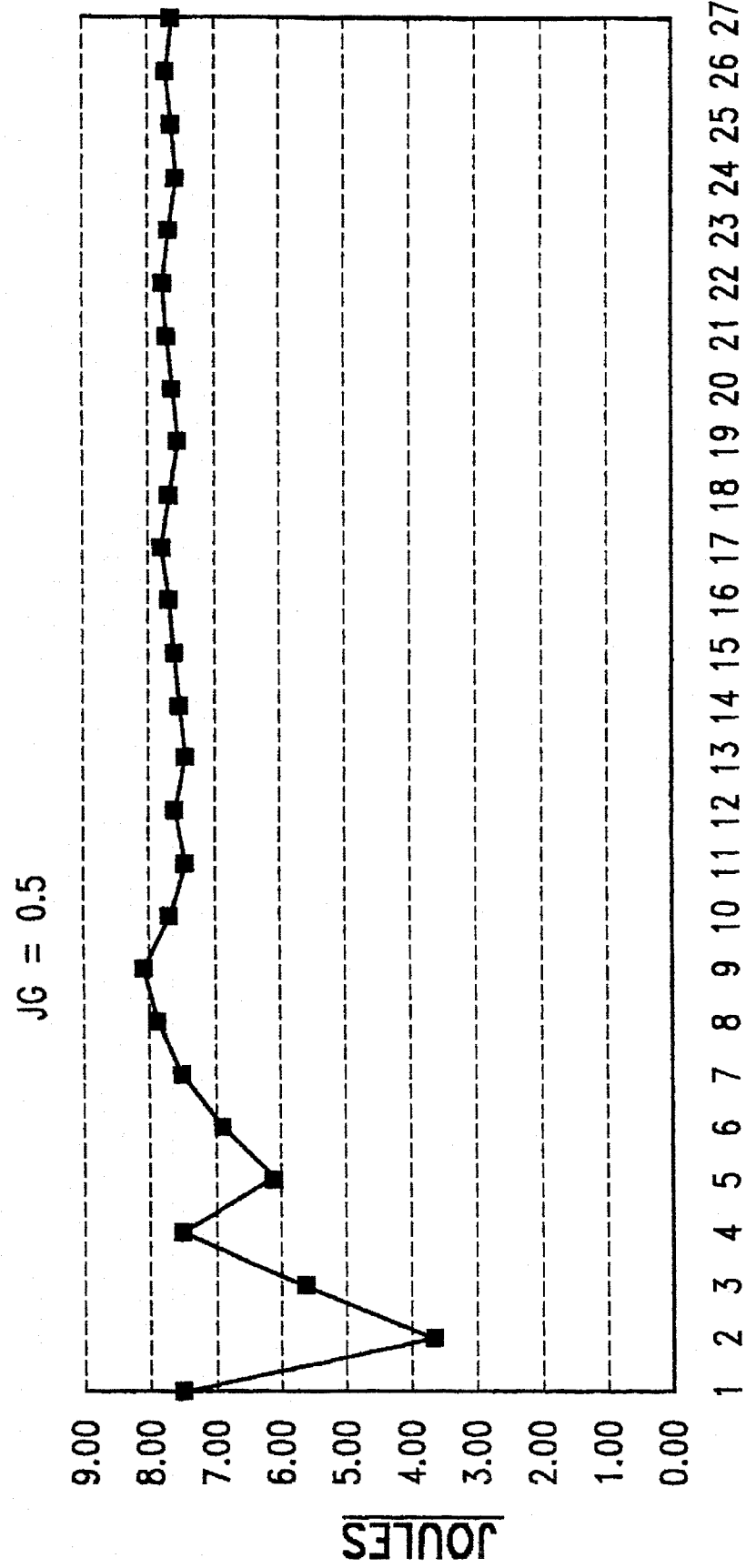
FIGS. 16 and 17 show a data table and graph, respectively, of estimated results using the method of the present invention, wherein the jump gain equals 0.5.
Figure 17:
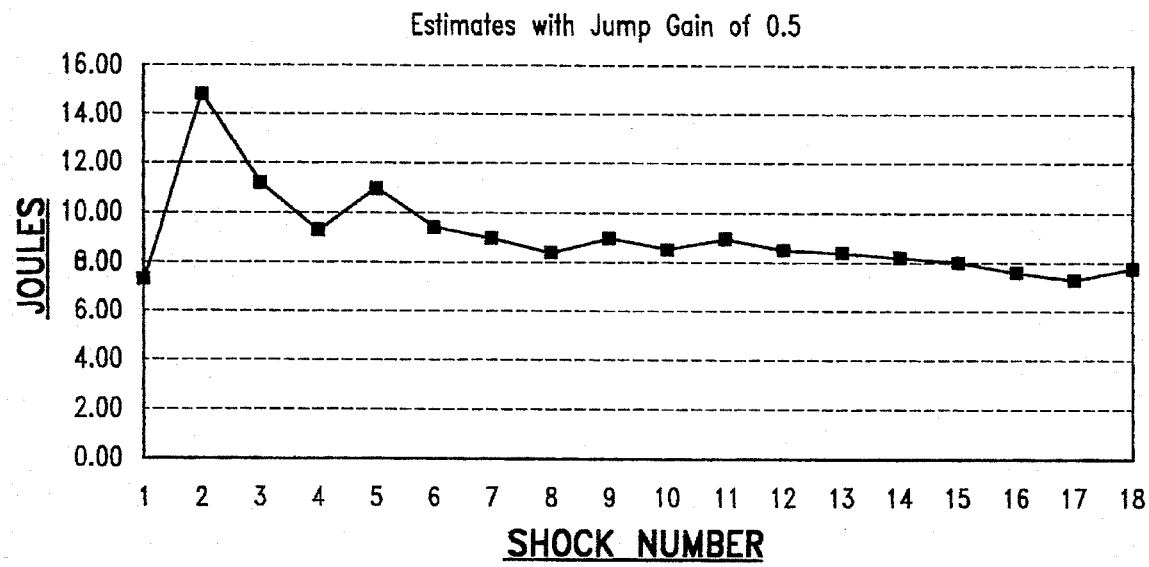
Figure 18:
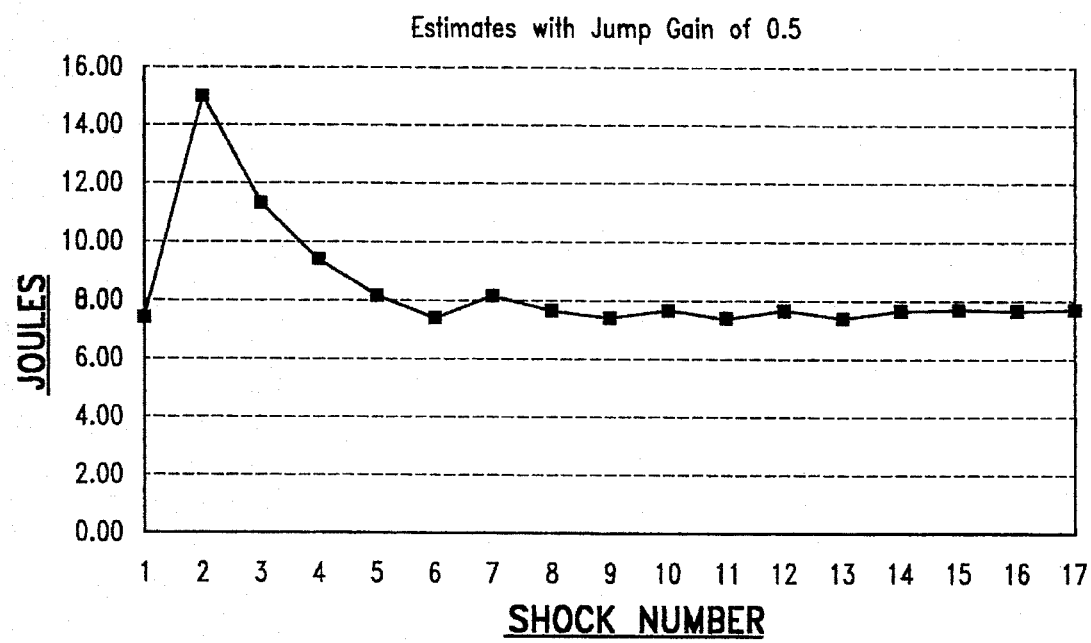
FIG. 18 is a graph showing a second run of the method wherein the jump gain equals 0.5.

FIGS. 16–18 show the results of two separate experimental examples using a jump gain of 0.5. It is noted that in both of these experiments the estimates are reasonably stable after the 7th shock and steadily converge to an 8 J estimate which is the true DFT.

Several variations on the basic method set forth above may be utilized to advance system performance consistent with the basic teachings of this invention. For example, medians could be used instead of means in the calculations. The value of the jump gain could also change during the course of the experiment. The doubling or halving that occurs in the initial stage of the shocks could change to a multiplication by a factor of 1.5 or division thereof. The important aspect of this invention is the basic convergence technique to derive the DFT. The prior art approaches rely on starting at a high level and moving down with one or two fixed step sizes, a process which is fundamentally different and inferior to the method of Applicants' invention which utilizes optimized step size criteria.

As many changes are possible to the embodiments of this invention utilizing the teachings thereof, the descriptions above, and the accompanying drawings should be interpreted in the illustrative and not the limited sense.

That which is claimed is:

1. A method for determining defibrillation thresholds, comprising the steps of delivering an initial shock series to a patient, said shock series comprising a number of shocks determined by delivering a first shock of a predetermined energy level, determining whether said first shock yields either a positive or negative defibrillation event, and delivering successive shocks of increasing energy levels until a positive defibrillation event is yielded if said first shock yielded a negative defibrillation event, and delivering successive shocks of decreasing energy levels until a negative defibrillation event is yielded if said first shock yielded a positive defibrillation event, determining an estimated shock level adjustment based on a statistical analysis of said initial shock series, and delivering at least one adjusted shock of a predetermined energy level based on said estimated shock level adjustment.

2. The method of claim 1, wherein said estimated shock level adjustment is further based on a relative number of positive and negative shocks delivered in said initial shock series.

3. The method of claim 1, wherein said energy level of each said successive shock is a factor of the level of its immediately preceding shock.

4. The method of claim 3, wherein said factor is two times the level of its immediately preceding shock in the case of an increasing energy level, and one-half the level of its immediately preceding shock in the case of a decreasing energy level.

5. The method of claim 1, wherein a single adjusted shock is delivered, and wherein the method comprises the additional step of determining whether said adjusted shock meets predetermined stopping criteria.

6. The method of claim 5, wherein the method concludes if said stopping criteria are met, said adjusted shock being a defibrillation threshold, and wherein a follow-up estimated shock level adjustment is determined based on said initial shock series and said adjusted shock, a follow-up adjusted shock is delivered and a follow-up stopping criteria determination is made if said stopping criteria are not met.

7. The method of claim 6, wherein said follow-up steps are continuously repeated until said stopping criteria are met.

8. The method of claim 5, wherein said stopping criteria is a based on a predetermined maximum number of shocks delivered by the system.

9. The method of claim 5, wherein said stopping criteria is based on a predetermined accuracy factor.

10. The method of claim 1, wherein a shock may yield a positive or a negative defibrillation event, and wherein said statistical analysis involves the step of adding a midpoint estimation and a jump factor, said midpoint estimation being an estimate of all previously delivered shocks, and said jump factor representing an adjustment away from said midpoint estimation.

11. The method of claim 10, wherein said midpoint estimation is determined by determining a mean of all negative defibrillation event shocks, determining a mean of all positive defibrillation event shocks, and by determining a mean of said determined negative mean and positive mean.

12. The method of claim 10, wherein said jump factor is determined according to:

$$\text{Jump Factor} = G_j(C_f/C_s - 1)(M_s - M_f), \text{ if } C_f \text{ is} \geq C_s; \text{ and}$$

$$-G_j(C_s/C_f - 1)(M_s - M_f), \text{ if } C_s \text{ is} > C_f,$$

wherein $M_f$=mean of negative defibrillation event shock energy levels, $M_s$=mean of positive defibrillation event shock energy levels, $C_f$=count of negative defibrillation event shocks, $C_s$=count of positive defibrillation event shocks, and $G_j$=jump constant.

13. The method of claim 1, wherein:

a) a number of shocks included in said initial shock series is determined by delivering a first shock of a predetermined energy level, determining whether said first shock yields either a positive or negative defibrillation event, and delivering successive shocks of increasing energy levels until a positive defibrillation event is yielded if said first shock yielded a negative defibrillation event, and delivering successive shocks of decreasing energy levels until a negative defibrillation event is yielded if said first shock yielded a positive defibrillation event;

b) a shock may yield a positive or a negative defibrillation event, and wherein said statistical analysis involves the steps of adding a midpoint estimation and a jump factor, said midpoint estimation being as estimate of all previously delivered shocks, and said jump factor representing an adjustment away from said midpoint estimation, said midpoint estimation being determined by determining a mean of all negative defibrillation event shocks, determining a mean of all positive defibrillation event shocks, and by determining a mean of said determined negative mean and positive mean, and wherein said jump factor is determined according to:

$$\text{Jump Factor} = G_j(C_f/C_s - 1)(M_s - M_f), \text{ if } C_f \text{ is} \geq C_s; \text{ and}$$

$$-G_j(C_s/C_f - 1)(M_s - M_f), \text{ if } C_s \text{ is} > C_f,$$

wherein $M_f$ = mean of negative defibrillation event shock energy levels, $M_s$ = mean of positive defibrillation event shock energy levels, $C_f$ = count of negative defibrillation event shocks, $C_s$ = count of positive defibrillation event shocks, and $G_j$ = jump constant; and c) the method comprises the additional steps of determining whether said adjusted shock meets predetermined stopping criteria, wherein the method concludes if said stopping criteria are met, said adjusted shock being a defibrillation threshold, and wherein a follow-up estimated shock level adjustment is determined based on said initial shock series and said adjusted shock, a follow-up adjusted shock is delivered and a follow-up stopping criteria determination is made if said stopping criteria are not met, and wherein said follow-up steps are continuously repeated until said stopping criteria are met, whereby successive shocks converge on the defibrillation by continuously varying estimated shock level adjustments.

14. A method for determining defibrillation thresholds, comprising the steps of:

a) delivering an initial shock series to a patient, said shock series comprising a first shock of a predetermined energy level which yields either a positive or negative defibrillation event, and at least one successive shock of an increasing or decreasing energy level, respectively, until either a negative or positive defibrillation event, respectively, is yielded;

b) determining an estimated shock level adjustment, said determination being made by adding a midpoint estimation and a jump factor, said midpoint estimation being as estimate of all previously delivered shocks, and said jump factor representing an adjustment away from said midpoint estimation;

c) delivering an adjusted shock of a predetermined energy level based on said estimated shock level adjustment, and d) determining whether said adjusted shock meets predetermined stopping criteria and concluding the method if said stopping criteria are met, said adjusted shock being a defibrillation threshold, and repeating steps (b)–(d), sequentially, if said stopping criteria are not met.

15. A method for determining defibrillation thresholds, comprising the steps of:

a) delivering an initial shock series to a patient, said shock series comprising a first shock of a predetermined energy level which yields either a positive or negative defibrillation event, and at least one successive shock of an decreasing or increasing energy level, respectively, until either a negative or positive defibrillation event, respectively, is yielded;

b) determining an estimated shock level adjustment, said determination being made by adding a midpoint estimation and a jump factor, said midpoint estimation being as estimate of all previously delivered shocks, and said jump factor representing an adjustment away from said midpoint estimation; said midpoint estimation being determined by determining a mean of all negative defibrillation event shock, determining a mean of all positive defibrillation event shocks, and by determining a mean of said determined negative mean and positive mean, said jump factor being determined statistically according to:

Jump Factor = $G_j(C_f/C_s - 1)(M_s - M_f)$, if $C_f$ is $\geq C_s$; and $-G_j(C_s/C_f - 1)(M_s - M_f)$, if $C_s$ is $> C_f$, wherein $M_f$ = mean of negative defibrillation event shock energy levels, $M_s$ = mean of positive defibrillation event shock energy levels, $C_f$ = count of negative defibrillation event shocks, $C_s$ = count of positive defibrillation event shocks, and $G_j$ = jump constant;

c) delivering an adjusted shock of a predetermined energy level based on said estimated shock level adjustment, and d) determining whether said adjusted shock meets predetermined stopping criteria and concluding the method if said stopping criteria are met, said adjusted shock being a defibrillation threshold, and repeating steps (b)–(d), sequentially, if said stopping criteria are not met, whereby the successive shocks converge on the defibrillation threshold by continuously varying said estimated shock level adjustments via a statistical analysis.

* * * * *